(12) United States Patent
Raguin et al.

(10) Patent No.: US 10,024,655 B2
(45) Date of Patent: Jul. 17, 2018

(54) AMBIENT LIGHT REJECTION FOR NON-IMAGING CONTACT SENSORS

(71) Applicants: Daniel H. Raguin, North Palm Beach, FL (US); John F. Carver, Palm City, FL (US)

(72) Inventors: Daniel H. Raguin, North Palm Beach, FL (US); John F. Carver, Palm City, FL (US)

(73) Assignee: CROSS MATCH TECHNOLOGIES, INC., Palm Beach Gardens, FL (US)

( * ) Notice: Subject to any disclaimer, the term of this patent is extended or adjusted under 35 U.S.C. 154(b) by 133 days.

(21) Appl. No.: 13/676,058

(22) Filed: Nov. 13, 2012

(65) Prior Publication Data

US 2013/0120760 A1    May 16, 2013

Related U.S. Application Data

(60) Provisional application No. 61/558,497, filed on Nov. 11, 2011.

(51) Int. Cl.
  *G01B 11/24* (2006.01)
  *A61B 5/117* (2016.01)
  *G06K 9/00* (2006.01)

(52) U.S. Cl.
  CPC .............. *G01B 11/24* (2013.01); *A61B 5/117* (2013.01); *G06K 9/0004* (2013.01)

(58) Field of Classification Search
  CPC ....... A61B 5/117; G06K 9/0004; G01B 11/24
  USPC .................................... 356/71; 382/115, 124
  See application file for complete search history.

(56) References Cited

U.S. PATENT DOCUMENTS

| | | | |
|---|---|---|---|
| 4,591,232 A | | 5/1986 | Jeskey |
| 4,783,167 A | * | 11/1988 | Schiller ................ A61B 5/1172 356/71 |
| 4,785,171 A | * | 11/1988 | Dowling, Jr. ...... G06K 9/00046 250/227.28 |
| 4,812,709 A | | 3/1989 | Dudasik |
| 5,416,573 A | | 5/1995 | Sartor, Jr. |

(Continued)

FOREIGN PATENT DOCUMENTS

| WO | WO 03/071345 | 8/2003 |
|---|---|---|
| WO | WO 20101051041 | 5/2010 |

OTHER PUBLICATIONS dpiX Technology, dpiX, LLC, printout from www.dpix.com/tech.html, 2010.

(Continued)

*Primary Examiner* — Dominic J Bologna
(74) *Attorney, Agent, or Firm* — Lukacher Law Group

(57) ABSTRACT

A sensor for capturing images of skin topology is provided having a platen, and a one or two-dimensional array of light sensing pixel elements for receiving light representative of skin topology when skin, such as finger(s), are present upon the platen. Such sensor being improved by structures, layers, or methods for reducing or blocking ambient light which would hinder the light sensing pixel elements from sensing the light representative of skin topology. The sensors are non-imaging contact sensors as they have platen to contact skin to be imaged, and do not require optics, such as lenses for focusing and/or magnification, to enable proper capture of light representative of skin topology on the sensor's light sensing pixel elements.

20 Claims, 8 Drawing Sheets

(56) References Cited

U.S. PATENT DOCUMENTS

| | | | |
|---|---|---|---|
| 5,737,071 | A | 4/1998 | Arndt |
| 5,812,252 | A * | 9/1998 | Bowker et al. ............... 356/71 |
| 5,828,773 | A | 10/1998 | Setlak et al. |
| 5,953,441 | A | 9/1999 | Setlak |
| 5,991,467 | A | 11/1999 | Kamiko |
| 6,175,641 | B1 | 1/2001 | Kallo et al. |
| 6,327,376 | B1 | 12/2001 | Harkin |
| 6,423,973 | B2 | 7/2002 | Choo et al. |
| 6,587,233 | B1 | 7/2003 | Salgado |
| 6,774,396 | B1 | 8/2004 | Chang et al. |
| 6,791,091 | B2 | 9/2004 | Rodricks et al. |
| 6,853,444 | B2 * | 2/2005 | Haddad ............. G06K 9/00033 356/71 |
| 7,369,690 | B2 | 5/2008 | Joo et al. |
| 8,077,929 | B2 | 12/2011 | Heidt |
| 2001/0030324 | A1 | 10/2001 | Morikawa et al. |
| 2003/0183019 | A1 | 10/2003 | Chae |
| 2004/0252867 | A1 * | 12/2004 | Lan et al. ..................... 382/124 |
| 2005/0025346 | A1 | 2/2005 | Higuchi |
| 2005/0229380 | A1 | 10/2005 | Deconde et al. |
| 2005/0249390 | A1 | 11/2005 | McClurg et al. |
| 2005/0281441 | A1 | 12/2005 | Martinsen et al. |
| 2006/0119837 | A1 * | 6/2006 | Raguin et al. ................ 356/71 |
| 2006/0120573 | A1 | 6/2006 | Lori |
| 2006/0140456 | A1 | 6/2006 | Foundeur et al. |
| 2006/0159314 | A1 | 7/2006 | Foundeur et al. |
| 2006/0217915 | A1 | 9/2006 | Dinh |
| 2008/0157921 | A1 | 7/2008 | Hendriks et al. |
| 2008/0253626 | A1 | 10/2008 | Shuckers et al. |
| 2009/0066345 | A1 | 3/2009 | Klauk et al. |
| 2009/0245603 | A1 * | 10/2009 | Koruga et al. ............... 382/128 |
| 2010/0001653 | A1 * | 1/2010 | Hilgers ........................ 315/149 |
| 2010/0246902 | A1 * | 9/2010 | Rowe et al. ................. 382/115 |
| 2012/0075425 | A1 * | 3/2012 | Thiel .................... A61B 5/0068 348/46 |
| 2012/0321149 | A1 | 12/2012 | Carver et al. |

OTHER PUBLICATIONS

R.L. Weisfield, M.A. Hartney, R.A. Street, and R.B Apte, "New Amorphous-Silicon Image Sensor for X-ray Diagnostic Medical Imaging Applications", Proc. SPIE Conf. on Physics of Medical Imaging, vol. 3336, pp. 444-452, 1998.

R. L. Weisfield, Amorphous silicon TFT X-ray image sensors, IEEE Int. Electron Dev. Meeting (IEDM 1998) Technical Dig., pp. 21-24, 1998.

3M Optical Systems, Vikuiti Anti-Reflection Film (AR), 2010.

L. Chen et al., Microstructured anti-reflection surface design for the omni-directional solar cells, Proc. SPIE, vol. 7046, 2008.

Rowe et al., Multispectral Fingerprint Image Acquisition, In: Advances in Biometrics, N.K. Ratha and V. Govindaraju (Eds), Springer, 2008.

\* cited by examiner

AMBIENT LIGHT REJECTION FOR NON-IMAGING CONTACT SENSORS

This application claims the benefit of U.S. Provisional Patent Application No. 61/558,497, filed Nov. 11, 2012, which is herein incorporated by reference.

FIELD OF THE INVENTION

The present invention relates to non-imaging contact sensors, and especially to non-imaging contact sensors which reduce the amount of or block ambient light upon the sensors. Such sensors are useful for fingerprint scanners, or for imaging any other skin topology or portion of skin (for example fingers, thumbs, palms, toes, etc.) regardless of whether ambient (natural and/or artificial) illumination is falling or not onto the sensors. The sensors are referred to herein as non-imaging contact sensors as they do not require optics (e.g., one or more lenses for focusing and/or magnification over the sensor's entire field of view) to enable proper capture of light representative of skin topology on the sensor's light sensing pixel elements. Such non-imaging contact sensors are enhanced in their performance by the present invention to provide improved sensors which reject all or a portion of ambient light which can otherwise negatively effect imaging performance of the sensor.

BACKGROUND ON THE INVENTION

Fingerprint sensing is now widely used for identification or verification purposes. For this, a person's fingerprint is acquired by a fingerprint sensing device whose output is processed and compared with stored characteristical data of one or more fingerprints to determine whether a match exists. Most fingerprint sensing employs an optical imaging technique, as illustrated schematically in FIG. 1. Light from a light source 12 is directed into a glass prism 10 via its face 10a onto a second prism face 10b which provides a platen 11 upon which finger(s) are placed, then by total internal reflection (TIR) the light reflected from the second prism face 10b passes through a third prism face 10c, is redirected via an optional field lens 13a and is then imaged by an objective lens 13b onto a two-dimensional (2D) sensor 14 (see e.g., U.S. Pat. Nos. 2,195,699 and 5,416,573). The field of view (FOV) of the objective lens 13b with aperture stop 16 is bound by the dash-dot-dash lines of 9a and 9b. Light coming from prism 10 that is inside this FOV will be imaged by the objective lens 13b towards the sensor 14 and light outside said FOV will not make it through the aperture stop and/or objective lens.

In using this optical imaging technique ambient light 18 is protected from being detected by sensor 14, in part, through three optical principles: imaging of total internal reflection (TIR) light; aperture stop 16 of the objective lens; and/or spectral filter 17. Since only TIR light is being imaged, outside light (i.e., ambient light) normally would not be imaged. For example, consider ambient light 18b which enters prism 10 via face 10b. After transmitting through prism 10 and exiting prism face 10a it is specularly reflected off of light source 12 and enters back into prism 10, reflects off of prism face 10b, emerges out prism face 10c and heads towards aperture stop 16 as ray 15b. Since all the reflections of the ambient light in the aforementioned example are specular, ray 15b is outside of the imaging system's FOV and said ray is therefore not detected by sensor 14. Alternatively for example, consider ambient light 18a that follows the same entry path as ray 18b, where ambient light 18a is scattered by light source 12 into dashed ray 19. Because the propagation angle of scattered light 19 is different from specular light, it is able to reflect off of prism face 10b and exit prism face 10c as ray 15a which is within the FOV of the system's aperture stop 16 and objective lens 13b.

Once light is imaged by the objective lens, it can still be blocked by a spectral filter 17. By way of example, if the illumination system for scanning fingerprints operates using 525 nm LEDs, such spectral filter may be a bandpass filter that passes only light between 500 and 550 nm. In this manner, red, infrared, and blue light comprising ambient light (e.g., such as that from overhead fluorescent light bulbs or the sunlight coming in through a window) is blocked and will not affect the light receiving (pixel) elements of the sensor 14.

Optically sensing of a fingerprint may also be performed using a photoelectric sensor 20 such as described in U.S. Pat. No. 5,991,467 or 7,369,690 which are incorporated herein by reference and shown schematically for example in FIG. 2. Backlight illumination 21a from a source 21 is transmitted to strike a finger 22 that is placed on a platen 23 and then light reflecting/scattering off of the finger 22 is detected by a two-dimension array of light sensitive detectors 24. The light sensitive detectors 24 each have a capacitor or capacitance which stores the accumulated charge of the detector 24 in accordance with the amount of the reflected light 25 the detector 24 receives. The amount of light received 25 into each of the light sensitive detectors 24 differs according to its position from which the light is reflected because a reflectance between a light reflected 25 from a ridge 8 portion that is protruded portion of the finger 22, and a light reflected from a valley 7 portion that is recessed portion of the finger 22, is different from each other, where the ridges and valleys of FIG. 2 have been drawn in an exaggerated scale in order to clarify the operation of the device.

Transistors 26 are provided for each of the detectors 24. Each transistor 26 switches to readout out the amount of the electron charge stored in the capacitor of its associated detector 24. The switching transistors 26 may be thin film transistors known as TFTs and light sensing detectors 24 may be thin-film based PIN photodiodes, Platen 23 may be provided by the surface of a thin protective layer 27 over a substrate or transparent backplane 29 having detectors 24, and other electronics, including transistors 26, electrical connections, and other elements, typical of TFT-based sensors for enabling their operation. Fabrication of sensor 20 may use amorphous silicon technology formed on a backplane 29 of glass. Backlight illumination 21 passes through substrate 29 and the non-opaque areas (e.g., areas that do not contain detectors 24, transistors 26, electrical connections and other elements) of substrate 29. Detectors 24 are opaque on the side facing substrate 29 so that illumination light 21a from source 21 cannot be directly detected, but only detected because of a reflection or scattering from the front side of sensor array 20a.

Detectors 24 are referred to hereinafter as light sensing pixel elements (or pixels) 24 of the two dimensional sensor array 20a, since each detector senses light in accordance with one pixel (when readout by other electronics on the chip of sensor 20) of a two-dimensional image representative of a fingerprint of the subject finger 22 or finger(s), palm, thumb, or other skin topology of a person. Since the finger 22 is in close proximity to the light sensing pixels of array 20a, no imaging optics are used (e.g., no objective lens, or other optics for focusing or magnification, and hence magnification of the light onto the array is one-to-one (1:1)).

Thus, the term of a device using this photoelectric sensor to capture a fingerprint image is referred herein as a non-imaging contact sensor 20, where such sensor has a two-dimensional sensor array 20a of light sensing pixels. Fingerprint contact sensors where TFTs provide transistors 26 are referred to herein as TFT-based fingerprint contact sensors. However, heretofore the improvements provided by the present invention, a commercially useful non-imaging contact fingerprint sensor has not been successfully developed for use in fingerprint scanners. Such being desirable since avoiding the need for imaging optics of a fingerprint scanner of FIG. 1 would enable the scanner to be more compact and lightweight, especially useful for mobile fingerprint scanners.

For a fingerprint sensor that is based upon a non-imaging contact approach as depicted in FIG. 2, one does not necessarily have those same principles with which to block ambient light 28. No TIR effects are utilized and since no imaging optics are used; there is no aperture stop to limit the field-of-view of light striking the light sensing pixels. Because of these facts, any of the light sensing pixels 24 of array 20a that are not directly underneath portions of the finger 22 placed on the platen 23, said light sensing pixels will be exposed and typically saturated by ambient light 28. Even the light sensing pixels of the sensor that are directly underneath the finger may also be affected by ambient light. The light sensing pixels 24 are exposed by ambient light 28 due to light striking pixels not shadowed by the finger and scattering off of switching transistors 26, light sensing pixels, or other electronics on the chip and scattering into the areas where the light sensing pixels 24 would normally be shadowed by the finger 22. Therefore, although at first glance, one might believe that due to the thin protective layer 27 (sometimes just a few microns of $SiO_2$ to protect the amorphous silicon) the finger will shadow at least the light sensing pixels 24 directly beneath, but this is not the case. It has been found that fingerprint images taken with a TFT-based non-imaging contact sensor of the type depicted in FIG. 2 with the room lights "off" provides an adequate fingerprint image, however when ambient light provided by room lights that are "on" is present, a significant amount of fingerprint image becomes saturated and lost. Such saturation worsens for fingerprint contact sensors that operate with outdoor ambient illumination, rather than room (artificial) light ambient illumination, since sunlight as generally significantly higher intensity than room light. It would thus be desirable to avoid this problem of saturation due to ambient light on non-imaging contact fingerprint sensors.

SUMMARY OF THE INVENTION

Accordingly, one object of the present invention is to provide non-imaging contact sensors which reduce the amount of, or blocks, ambient light upon light sensing pixel elements of the sensors.

It is another object of the present invention to provide non-imaging contact sensors which block or reduce ambient light when present so as to improve imaging by such sensors when utilized in fingerprint or other skin topology scanners.

A further object of the present invention is to provide non-imaging contact sensors having illumination for the fingerprint sensor which is provided from either underneath the sensor, or above the sensor.

A still further object of the present invention is to provide non-imaging contact sensors which block ambient light from saturating the light sensing pixels of the fingerprint sensor.

Briefly described, the present invention embodies a sensor for capturing images of skin topology, such as one or more fingers, having a platen, a one or two-dimensional array of light sensing pixel elements for receiving light representative of skin topology of skin when present upon the platen, and one of more structures or layers of material for reducing or blocking ambient light which would hinder the light sensing pixel elements from sensing the light representative of skin topology.

Such structures or layers of material may consist of one or more of: a neutral density filter; one or more anti-reflective coatings one or more coatings which reflect or absorb wavelengths of illumination at certain angles of incidence; one or more coatings to reflect or absorb wavelengths of ambient light illumination; one or more polarizing layers; one or more structures along the sides of each one of the light sensing pixel elements for limiting the direction of the path of the ambient light with respect to the light sensing pixel element; micro-optics registered with the light sensing pixel elements that limit the field-of-view of the light sensing pixel elements to the light representative of skin topology; a directional filter over the light sensing pixel elements; an optical element (or spectral filter) which shields the light sensing pixels to ambient light at wavelengths or angles of incident outside of the one or more selected sensor light sensing wavelengths or angles of incidence upon the light sensing pixel elements; a shield disposed with respect to the platen having material that blocks the ambient light; or a shield disposed with respect to the platen having material to absorb the portion of the ambient light at wavelengths of operation of the light sensing pixel elements.

The light sensing pixel elements of the sensor are disposed upon a substrate having a protective layer, where the platen is provided by one of the upper surface of the protective layer or one of such structures or layers that reduce or block ambient light (e.g., anti-reflective coating, or spectral filter) that may be present upon said protective layer. The light sensing pixel elements each comprise a photo-detecting element (such as a photo-detector) and an associated switching element (such as a TFT) for reading signals representative of light detected by the photo-detecting element.

The sensor further has a source for illuminating the platen via the substrate, such that light representative of skin topology represents a reflected portion of the illumination upon the platen unblocked by opaque items on the substrate representing at least the photo-detecting element and switching element of each of the light sensing elements. The light sensing pixel elements of the sensors although preferably utilizes TFTs, may use other types of array of light sensing pixel elements such as those of a large area CMOS or CCD.

In operation, only a portion (active area) of the overall area of each of the light sensing pixel elements receives the light representative of skin topology. Optionally, this portion with respect to the overall each of each light sensing pixel element is selected in the sensor to reduce the amount of ambient illumination received by the array when such ambient illumination is present in relation to the amount of desired light illuminating the platen. Although this reduction of the active area of the pixel elements may reduce sensor array sensitivity to light representative of skin topology, it has the benefit of reducing the risk of light sensing elements becoming saturated by ambient light if present in amount which otherwise saturate the sensing elements. For the case of a non-imaging contact sensor that is constructed on a transparent backplane, reduction in the pixel active area allows for more of the pixel element to be transparent, thereby enabling more light in the case of backside illumination to preferably illuminate the platen surface as opposed to ambient light that might be present. Preferably, the percentage of the active area with respect to the overall area of each light sensing pixel element is less than 40% as compared to typical TFT-based light detecting sensors used in X-ray devices that strive for 80-100% active area. To achieve such high active area percentages in TFT-based digital X-ray devices, sometimes requires the electronics of the pixel (e.g., transistors) to be placed underneath the photodiode of the pixel. Although the pixel electronics of the present invention are illustrated in the Figures as being next to the light sensitive portion of the pixel, it is understood that the electronics may also be underneath the photodiodes, thereby enabling even more of the pixel area to be transparent, thereby further increasing the amount of desired light in ratio to ambient light that is detected. Such selected reduction of the pixel active area may be provided with or without the above described structure(s) or layer(s) of material disposed in the path of ambient light for reducing or blocking ambient light.

The sensor may be considered as an integrated sensor assembly having one or more layers of materials upon the substrate having electronics of the sensor including at least the light sensing pixels elements. Preferably, one of such layers integrated in the sensor assembly includes a spectral filter for blocking wavelengths of light the sensing elements are sensitivity to, but where said blocked light wavelengths are not used as part of the desired illumination of the object in contact with the platen. Said layers may also block light wavelengths that are part of the desired light illumination, but substantially for those angles of incidence (AOI) that are not part of the desired illumination AOI. By way of example, if 525 nm LEDs are the desired illumination and they illuminate the platen with a cone angle of ±15°, then spectral and blocking layer constructed of dielectric and/or absorptive layers may block ambient light wavelengths that are <500 nm, >550 nm and for wavelengths between 500 and 550 nm, block only those light rays incident at angles >15°. Such one or more layers are integrated together into a unitary structure providing the sensor in a manner similar to an ASIC chip assembly. Optionally, the sensor operates (to illuminate the platen and sense light on pixel element) in a spectral region of wavelengths where there is little ambient light.

The sensors of the present invention may be provided in a scanner housing having a processor for receiving signals from the light sensing pixel elements representative of the light received by the light sensing pixel elements.

The non-contact sensors shown in the figures have been simplified for purpose of illustration, and thus are drawn schematically to show their operation. Examples of light or illumination described in connection with figures are depicted as arrows or ray lines.

BRIEF DESCRIPTION OF THE DRAWINGS

The foregoing and other objects, features and advantages of the invention will become more apparent from a reading of the following description in connection with the accompanying drawings in which.

DETAILED DESCRIPTION OF THE INVENTION

Figure 1:
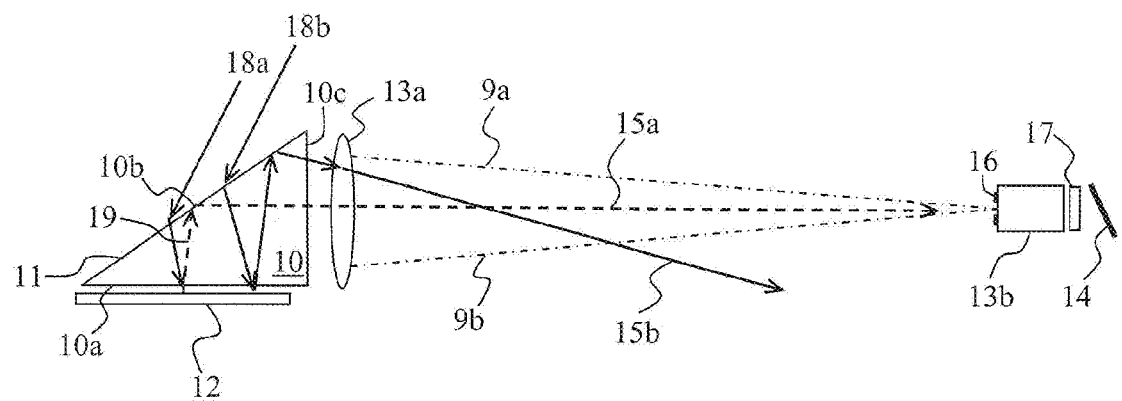
FIG. 1 is schematic diagram illustrating the prior art for a TIR prism-based fingerprint scanner.
Figure 2:
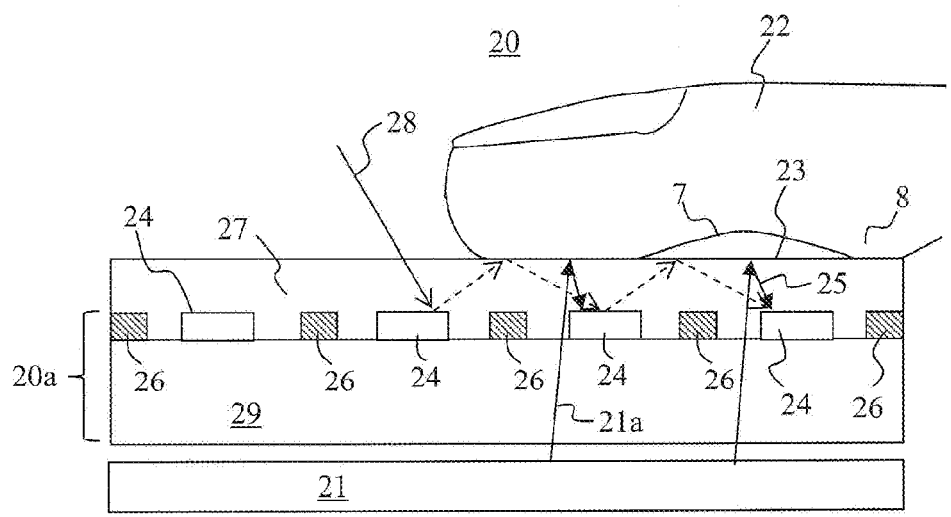
FIG. 2 is a schematic cross-section of part of a TFT-based sensor of the prior art, showing such use in the case of imaging a fingerprint.

Multiple different mechanisms and methods are provided by the embodiments of the present invention for restricting the amount of ambient light detected by non-imaging contact sensors utilizing or modifying a 2D TFT-base sensor, such as shown for example in FIG. 2, to improve its performance in fingerprint scanning or imaging applications. Ambient light represents illumination from one or more of artificial (e.g., room illumination) or natural illumination sources (e.g., sun light) outside of housing 116 (FIG. 13) with such sensors of the present invention. The improved sensors described in such embodiments may be based on a 2D TFT array such as manufactured by DPIX of Palo, Alto, Calif., U.S.A. These DPIX 2D TFT arrays range in area from 2" by 2" to 19" by 19" with 100-200 μm resolution, and are currently used in digital x-ray scanners, but heretofore are not believed utilized in a sensor for a fingerprint scanner. For example, a DPIX flat panel amorphous Silicon (a-Si) x-ray image sensor may have a 30×40 cm² active area, 127 μm resolution, and 7.4 megapixels. For more information on DPIX arrays and sensors, see for e.g., R. L. Weisfield, M. A. Hartney, R. A. Street, and R. B. Apte, "New Amorphous-Silicon Image Sensor for X-Ray Diagnostic Medical Imaging Applications", SPIE Vol. 3336, Medical Imaging 1998. Physics of Medical Imaging, 22-24 Feb. 1998, pp. 444-452. Other photoelectric sensors which are non-imaging utilize CMOS sensors, such as manufactured by Dexela in London, England. Although each embodiment is set forth separately, two or more of the embodiments may be combined to provide a desired amount of ambient light rejection.

Figure 3A:
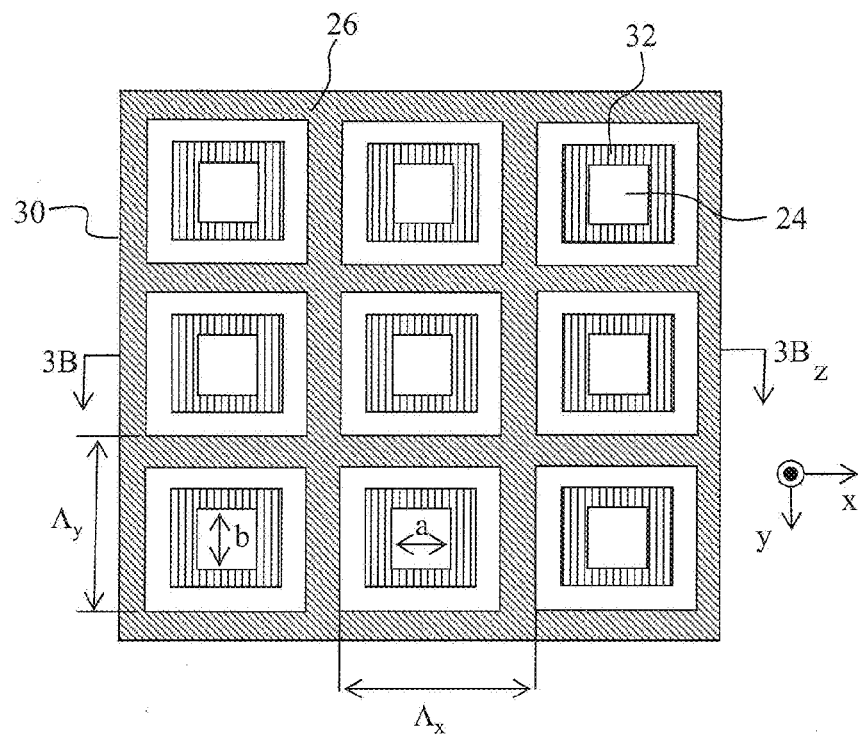
FIG. 3A is a top-down schematic view of a portion of a two-dimensional (2D0 TFT-based sensor array in accordance with a first embodiment of the present invention having light barriers along the outside of each of the light sensing pixels of the sensor.
Figure 3B:
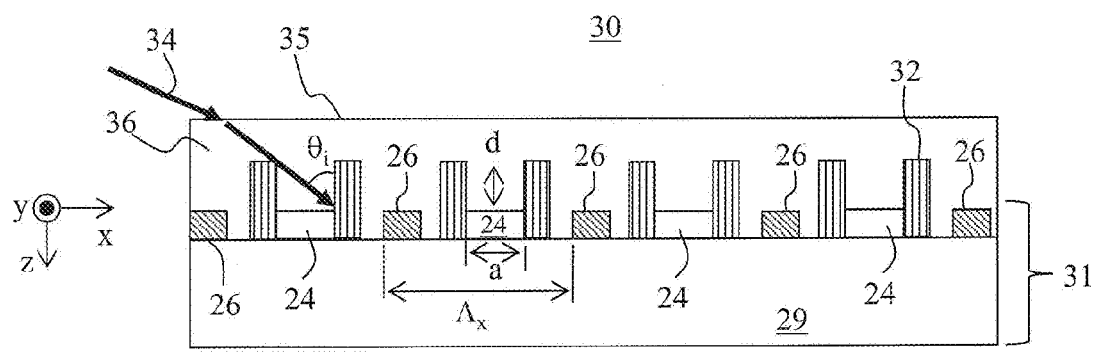
FIG. 3B is a cross-section of the sensor of FIG. 3A along lines 3B-3B of FIG. 3A.

Referring to FIGS. 3A and 3B, a non-imaging contact sensor 30 in accordance with a first embodiment of the present invention is shown having a two-dimensional array 31 of light sensing pixel elements (or pixels) 24 which is the same or similar as shown in array 20a as described earlier with the improvement of each light sensing pixel 24 having a light barrier (or wall) 32 surrounding its photosensitive region or area. Each light barrier 32 may be constructed of material(s) that are opaque to at least some of the wavelengths the light sensing pixel 24 is sensitive to and such light barrier 32 extends above the photosensitive region a distance "d" and barrier 32 helps restrict ambient light 34 from being detected by the light sensing region 24 of width "a" and height "b". In such a manner, as illustrated in the x-z plane of FIG. 4B, light that propagates at an angle of $\theta_i$ is blocked from exposing the light sensing pixel 24. By way of example if the width of the light sensitive region 24 in the x direction "a" is 20 μm and the height "b" is 40 μm, then ambient light coming in at angles >26.6 degrees will be blocked. The physical blocking features provided by light barrier 32 about each of light sensing pixels 24 of the sensor array 31 thus limit the direction that ambient light 34 can be detected by each of the light receiving pixel 24 received via platen 35 provided by the surface of the protective coating 36. The operation of sensor 30 otherwise may be the same as described earlier in connection with FIG. 2.

For purposes of illustration in FIG. 3A, diagonal cross-hatched areas outside of the sensing pixels 24 on the front surface of substrate 29 are denoted as 26 to show the regions along substrate 29 which include at least switching transistors, data lines, and other electronics enabling operation of sensing pixel elements 24 (e.g., control and readout as typical of TFT-based sensor arrays such as described earlier). Such area outside of pixel elements 24 and walls 32 have paths unblocked by any components on substrate 29 enabling a portion of the non-ambient light 21 to reach platen 35 to enable sensor 30 operation.

The light barriers 32 may be fabricated using photolithography during the fabrication of the sensor array 31 or may be fabricated independently of the array and then placed on top of the array registered over areas 24 of the array. The light barrier 32 may have a pitch exactly equal that of the sensor 24 pitch in which case it may be critical to align the two relative to each other, or the pixel pitch of the light barrier 32 may be significantly smaller than that of the sensor pixel 24, in which case relative alignment to the sensor pixels 24 is not as critical. For purposes of illustration the light barriers 32 are shown square shaped in FIG. 3A, but they may be other geometric shape, such as circular or triangular.

By way of example, Vicuiti™ films based upon micro-louver technology such as marketed by 3M (St Paul, Minn.) can be used to restrict the ambient light field of view seen by the sensor array as well as technology described in U.S. Pat. No. 4,812,709. For example, light barrier 32 may be provided by Vicuiti™ films along a TFT sensor area, such as the TFT-based sensors manufactured by DPIX. Such microlouver, or other light barriers 32, may be provided such that it only passes light about the surface normal (e.g., 0°±30°), or passes light about an off-axis angle (e.g., 30°±20°), depending upon the direction the illumination light approaches the sensor array.

As stated earlier, sensor arrays 20a of FIG. 2 may be fabricated using thin-film transistor (TFT), CMOS or other technology. Regardless of the technology used to fabricate the 2D optical sensor array 20a, there will be photosensitive regions 24 as well as regions that are used for the pixel and drive/read electronics, which includes but is not limited to transistors 26. For fingerprint scanning applications, the desire is to have ≥250 ppi (points per inch) for low-security biometric applications (e.g., computer or cell-phone logins) and ≥500 ppi for fingerprint applications involving AFIS (Automated Fingerprint Identification System) databases where hardware scanner certifications are required by organizations such as the United States (U.S.) Federal Bureau of Investigation (FBI). By way of example, for a fingerprint scanner that must be FBI-certified for 500 ppi resolution, the pixel pitch in the x and y directions, ($\Lambda_x$ and $\Lambda_y$, respectively) may be set equal to 50.8±0.5 μm (500 ppi±1%) or may be set to a smaller pixel pitch, for example 40 μm (635 ppi) and the final image downsampled to 500 ppi before it electronically enters the AFIS database.

Considering FIG. 3A geometry with or without the light barriers, the fill factor of the sensor array 31 is defined by the ratio of the active area ("a" by "b") of the light sensing pixel 24 divided by the total area ($\Lambda_x$ by $\Lambda_y$) of the site, which is equal to $a \cdot b/(\Lambda_x \cdot \Lambda_y)$. The current market for large-pixel, large-area sensors is the digital X-ray market. Large-pixel (>70 μm), large area (>2" square) sensors fabricated with a scintillation layer (see, for example TFT-based sensors fabricated by DPIX of Palo Alto, Calif. or CMOS-based sensors by Dexela Limited of London, England), have as large a fill factor as possible since the X-ray source is not very intense (for health reasons), the X-ray to green light conversion efficiency of the scintillation layer is not particularly efficient, and ambient light (containing X-ray radiation) is not a concern. In fact some companies for digital mammography imaging where pixels tend to be the smallest of any digital X-ray application (typically in the 70 to 100 μm range), have developed TFT sensor fabrication technology wherein the PIN photodiode is fabricated on top of the pixel transistors and drive/read lines, thereby allowing for essentially 100% fill factor. Reducing the fill factor is thus contrary to the typical use of large area sensor arrays for producing digital X-ray images as well as high-end photography (terrestrial and space), since both applications require maximum sensitivity and therefore maximum sensor fill factor.

However, in accordance with a second embodiment of the present invention for fingerprint scanning applications, the reverse of the current trend for high fill factor is provided, namely that because of the possibility of the light sensing regions 24 being saturated by ambient light and because a TFT sensor for fingerprint scanning may be backlit (as opposed to digital X-ray applications where the sensor is always front lit), that the fill factor of the sensor array may be purposely reduced and in fact be in the region of <40%, or even <30% or <20% if needed to reduce the amount of ambient illumination received by the sensor array when such ambient illumination is present despite the loss of sensor array sensitivity. Thus, according to this embodiment, pixels with a fill factor (sensitive pixel area to total pixel area) smaller than 40% may be selected for manufacture of the sensor array.

Figure 4:
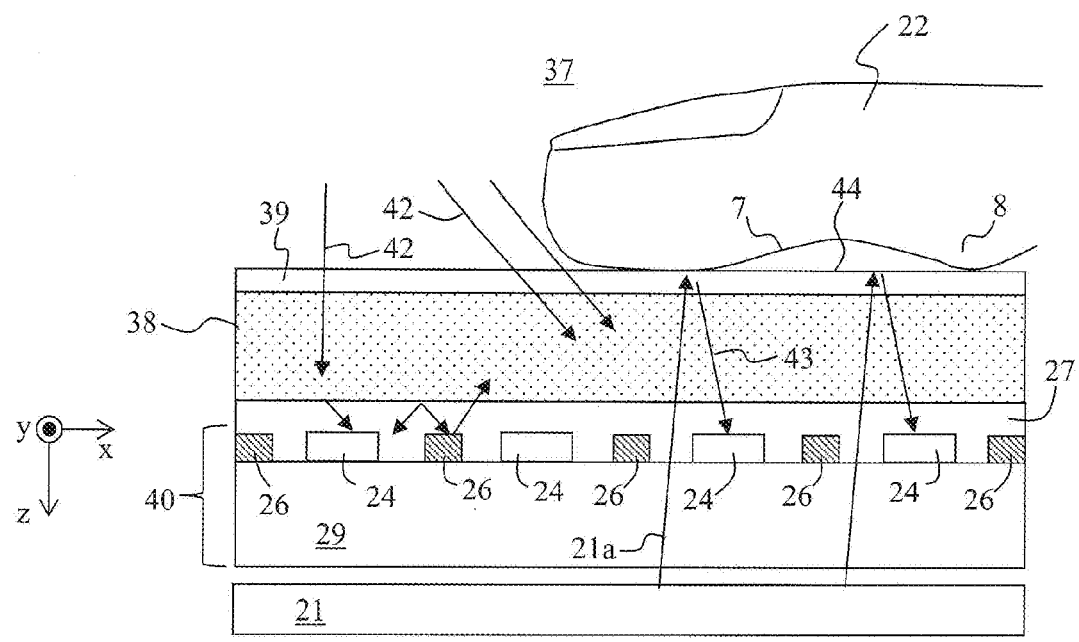
FIG. 4 is a schematic cross-section of a portion of 2D TFT-based sensor in accordance with a third embodiment of the present invention having coating layer, ND filter, or polarizing materials for ambient light rejection.

Referring to FIG. 4, a third embodiment of the present invention of a non-imaging contact sensor 37 is shown having two additional layers 38 and 39 on top of a protective layer 27, otherwise the sensor array 40 is the same or similar to sensor array 20a described earlier. A platen 44 in sensor 37 is provided by the surface of layer 39. Layer 38 provides one of a neutral density (ND) filter, a polarizing material, or a combination thereof. Although an ND filter will reduce both the ambient light 42 and the signal light 43, the purpose is to reduce the light level such that for a given integration time of the light sensitive pixels 24, the full-well depth of the detectors are not reached (in other words, the sensor pixels do not get saturated). Additionally there is a benefit of increased signal-to-noise-ratio (SNR) in that ambient light that "tunnels" underneath the finger as a result of multiple scattering/reflection events will traverse through a longer path length through layer 38 than the illumination light and thereby suffer more absorption. For example, if layer 38 is 5 µm thick and the period of sensor array is 50 µm (i.e., center-to-center spacing of light sensing pixels 24), then an illumination ray from backlight illumination propagates approximately 10 µm through the ND filter while ambient light scattering from a neighboring pixel will propagate 50 µm or more to reach underneath a skin topology and expose neighboring pixels, therefore being absorbed at the rate of the aforementioned illumination ray raised to the $5^{th}$ power. Thus, use of a neutral density filter layer enables an increase of the reflected fingerprint sensing light to a point that it can overcome the ambient light without saturating the sensor pixels.

Layer 38 may also or instead incorporate a polarizer to reduce the amount ambient light 42, but preferentially over the fingerprint signal light 43. For example, if there is no coating layer 39, then more p-polarized light will enter the device than s-polarization due to the differences in the respective Fresnel reflections. Therefore, if the polarizer is a linear polarizer that blocks p-polarized light, then ambient light 42 will be preferentially blocked over the fingerprint illumination light 21a which optionally could be s-polarized. A polarizer will also help to minimize scattered light that reflects and works its way under the finger since scattered light tends to be depolarized. In other words, given that ambient light that comes into the sensor 37 at increasingly oblique angles, such ambient light 42 is increasingly p-polarized due to the Brewster's angle effect. Therefore by having the fingerprint illumination directed at close to normal incidence, more of the ambient light (which is more oblique) will be blocked by the polarizer even if the fingerprint illumination 21a is not polarized.

The second optional layer 39 is a coating layer which may incorporate a spectral absorptive layer, a dielectric layer stack, a hologram or any combination thereof. Through the use of a spectral absorptive layer, light that the light sensitive detectors are sensitive too, but are not being used for fingerprint sensing are absorbed. For example, if the light sensitive pixels 24 of the sensor array 40 are fabricated based on CMOS technology, it may be sensitive to wavelengths from 350 to 1100 nm. If the fingerprint scanner 37 operates only at wavelengths of 500 to 550 nm, then the absorptive material would preferentially pass only green light. Similarly, if a dielectric stack is used, then it transmits only green light band and reflects wavelengths outside of this band that the light sensitive detectors are sensitive to. Layer 39, in addition to passing selective wavelengths, may avoid transmitting ambient light of angles and/or polarizations other than those used by signal light 21a. Other than the reduction or elimination of ambient light on light sensing pixels 24 by coatings 38 and 39, the operation of sensor 37 is otherwise the same as described earlier in connection with FIG. 2. In other words the coating 39 provides a bandpass filter, such as can be fabricated by a number of optical coating vendors including Semrock, Inc. (Buffalo, N.Y.) or Iridian Spectral Technologies (Ottawa, Ontario, Canada). In addition or in lieu of layers 38 and 39, a hologram may be incorporated in to the protective layer 27. The hologram reflects light of a certain spectral content, field-of-view, and polarization. Such holograms may be fabricated in materials, such as dichromated gelatin (DCG) or photopolymers, such as those produced by Bayer MaterialScience (Leverkusen, Germany).

Figure 5:
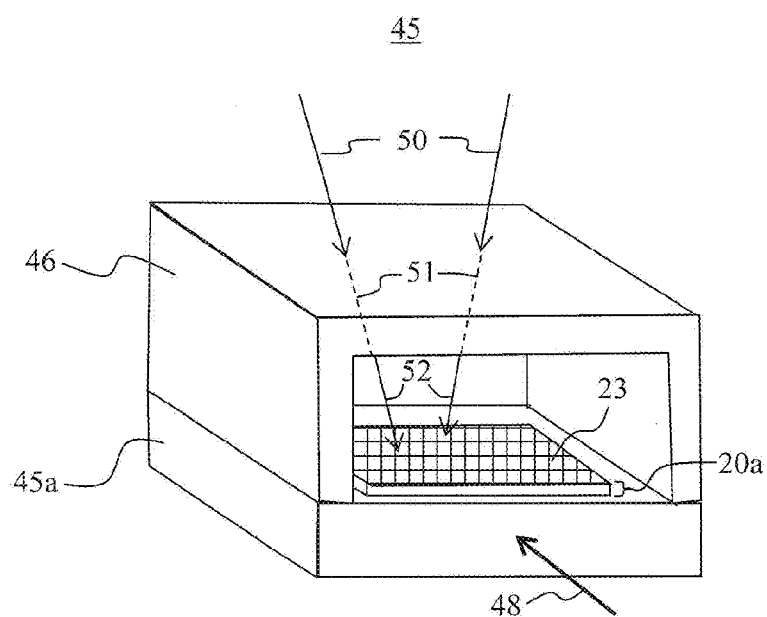
FIG. 5 is a perspective view of a fingerprint scanner using a TFT-based sensor in accordance with a fourth embodiment of the present invention in which a light shield is provided over the sensor for ambient light rejection.

Referring to FIG. 5, a fourth embodiment of the present invention of a non-imaging contact scanner 45 is shown having light shield 46 over a sensor 20 which is disposed in a housing 45a. The ambient light shield 46 preferably is mounted above the fingerprint capture platen 23 such that finger(s) may be placed on top of the scanner platen 23 without any hindrance in the direction shown by arrow 48. The platen 23 may for example be the top surface of the protective coating layer 27 of FIG. 2. The shield 46 may block all ambient light 50 the light sensitive pixels 24 of the array 20a are sensitive to, however, in order to still provide the user some view of his/her fingers, the shield may only absorb the wavelengths of operation of the sensor 20 and let pass other wavelengths of light as shown by line 51 and then arrow 52. Such a colored light shield operates best if the protective coating layer 27 of the scanner 45 absorbs or reflects wavelengths of light not used to detect and/or image the fingerprint. By way of example, for a sensor 20 operating in the visible green spectral region, the ambient light shield 46 may block green only light and therefore look purple since it passes red and blue wavelengths. In this example, light-sensitive pixels 24 are not sensitive to red and blue transmitted light, or coating 27 blocks said wavelengths. Thus, the ambient light shield 46 may block all visible light or, in order to aid in the subject being able to see where his/her fingers are being placed, may be tinted such that the light shield blocks wavelengths of light used in the scanning of the fingerprint. The visible light not blocked allows the user to view his/her fingers through shield 46 and is then preferentially blocked by one or more spectral filters, such as described below. Although the platen 23 of sensor 20 is shown in FIG. 5, the platen and sensor may be in accordance with any other of the embodiments described herein.

Figure 6:
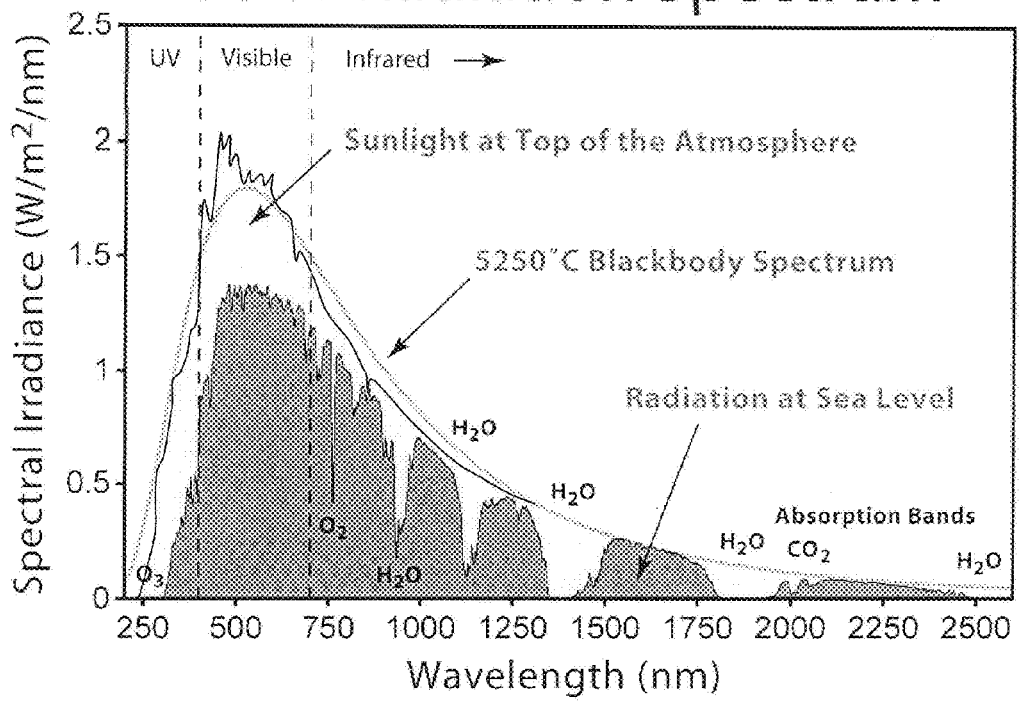
FIG. 6 is a plot of the solar radiation spectrum.
Figure 7:
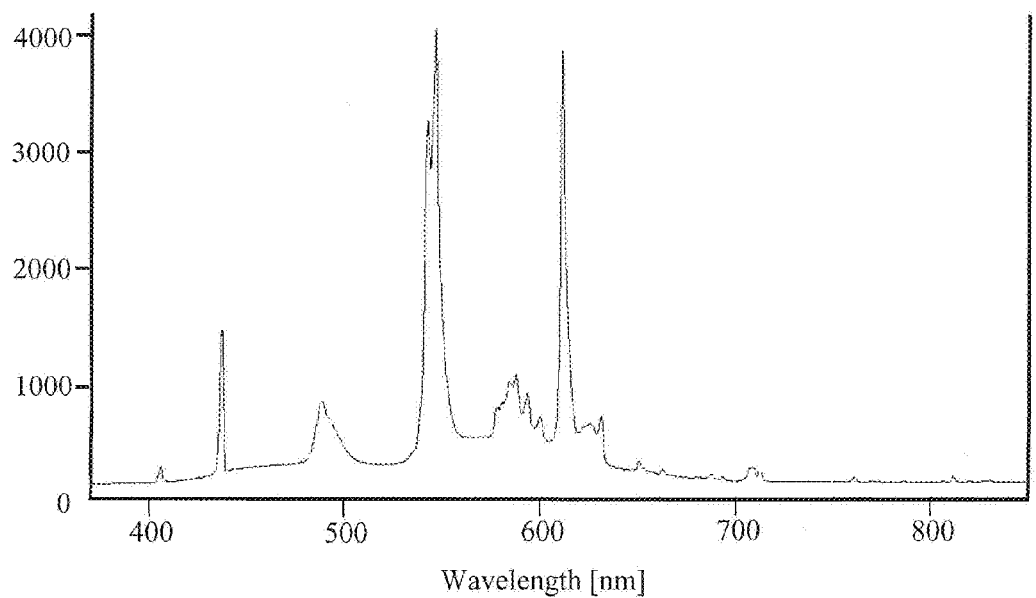
FIG. 7 is a plot of the output intensity over the spectrum of a typical fluorescent light bulb.

It is a fifth embodiment of the present invention that the fingerprint scanner's wavelength of operation of its light sensing pixels 24 of sensor 20, or any other of the sensors of the other embodiments, is in a spectral region where there is little ambient light. Illustrated in FIGS. 6 and 7 are the spectra for sunlight and for fluorescent lights, respectively (obtained from www.wikipedia.com). For a contact optical fingerprint scanner operating primarily in be presence of fluorescent lights, the preferred wavelengths of operation from an ambient rejection standpoint may for example be in the <430 nm, 450-480, 500-530, or >650 nm spectral regions. For a contact optical fingerprint scanner operating in sunlight or outdoor light, it is preferential if the device operates in the ultraviolet (UV), violet, or >750 nm (near infrared) portions of the spectrum. If possible, operating at the 760 nm $O_2$ or 950 nm $H_2O$ spectral hole is preferred. Thus by using a spectral filter that passes only the wavelength range of the fingerprint illumination, all other wavelengths of the ambient light will be blocked. For example if the fingerprint illumination 21a is in the 500-550 nm range, a spectral filter can be used to block out ambient light below 500 nm (e.g., blue and violet light) as well as wavelengths greater than 550 nm, such as yellow, orange, red and infrared light that the light sensitive detectors of the sensor array might be sensitive to. Thus in references to FIG. 2 the improvement is providing illumination from source 21 and sensitivity of light sensing pixels 24 to wavelength(s) or band(s) where there is little ambient light, such as in the UV range, or providing in layer 39 a spectral filter in the path of light from source 21 selected to block light outside of the desired wavelength(s) or range(s).

Figure 8:
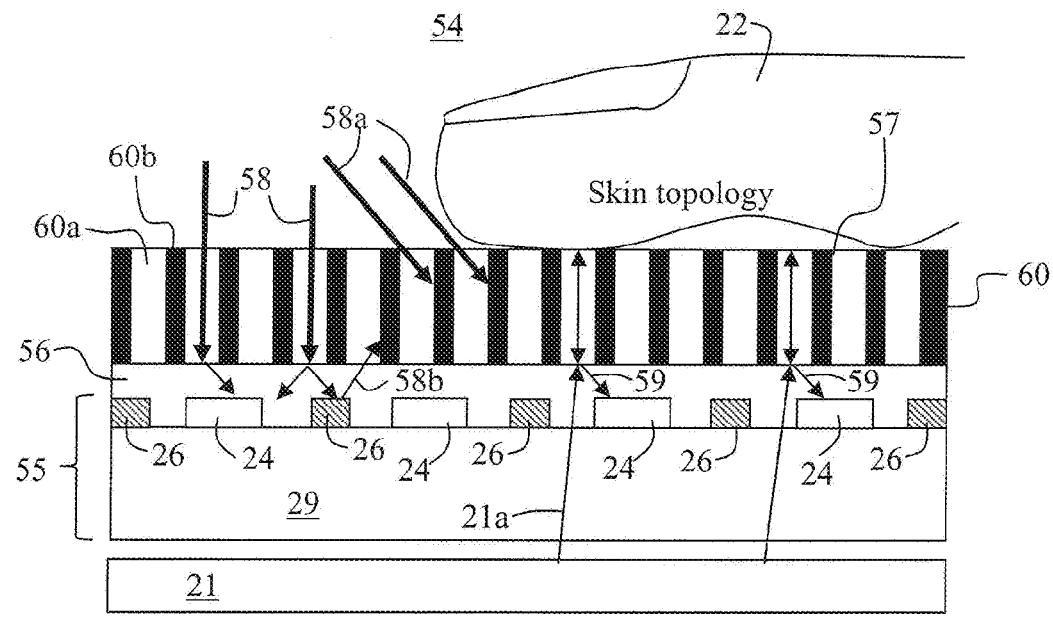
FIG. 8 is a schematic cross-sectional view of a portion of 2D TFT-based sensor in accordance with a sixth embodiment of the present invention having a fiber-optic plate (FOP) for ambient light rejection.

Referring to FIG. 8, a sixth embodiment of the present invention of a non-imaging contact sensor 54 with a two-dimensional sensor array 55 and protective coating 56 which may be the same or similar to sensor array 20a and coating 27 described earlier. Though other sensor technologies and other illumination may be used, as illustrated, the fingerprint scanner 54 comprises a 2D array 55 of sensory pixels arranged on a transparent backplane 29 with a certain percentage of transparent area, thereby allowing light 21a from a backlight 21 to illuminate a finger 22 that is placed on a platen 57 at the top of the sensor 54. By way of example, the sensor array 55 may be a thin-film technology (TFT) array of sensors fabricated using amorphous silicon technology on a backplane 29 of glass. In order to block ambient light 58 from being detected by light sensing pixels 24 that are beneath the finger, a fiber-optic face plate (FOP) 60 is placed on top of the protective layer 56, where said placement is preferentially performed with the aid of an adhesive, epoxy or some other affixation means, thereby removing any air or air bubbles from the boundary between the FOP 60 and the protective layer 56.

This FOP 60 is composed of fibers 60a with light absorbing regions or material 60b in between the fibers 60a. The 2D arrays of fibers 60a guides light 21a from the light source 21 to platen 57, via substrate 29 and non-opaque regions of array 55, and reflected light from platen 57 representative of finger skin topology (or fingerprint) is guided by fibers 60a down to light sensing pixels 24. The fibers 60a may be packed in a 2D rectilinear or hexagonal array with material 60b in between the fibers. For example, absorbing regions 60b may incorporate black glass, such as is typically used by in FOPs manufactured by INCOM, Inc. (Charlton, Mass.) and Schott North America, Inc. (Southbridge, Mass.). The absorbing regions 60b prevent light 58 that is not guided by the fibers 60a from propagating at oblique angles and finding its way underneath the finger 22 and being detected and potentially saturating the light sensing pixels 24 otherwise shadowed by the finger 22. This absorption of light prevents both direct ambient light 58a and scattered ambient light 58b from propagating obliquely and going underneath the finger 22, which would otherwise disrupt the fingerprint from being imaged. In this manner light entering into the FOP within the acceptance cone of the fibers 60a is guided down. However, any ambient light entering at angles outside of the acceptance angle of the fibers 60a is not guided by the fibers 60a and is instead propagating into the interstitial black material 60b between the fibers and absorbed. The FOP 60 may specifically relate the fiber 60a pitch to the pixel pitch of the light sensing pixels 24 and therefore optimal operation is achieved with specific alignment of the FOP fibers 60a to the light sensing pixels 24 of the sensor 54. Alternately, the FOP 60 may have fibers 60a that are sufficiently small that many fibers fit above a single light sensing pixel 24. For example, FOPs made by INCOM contain 6 μm fibers and therefore in a 500 ppi sensor array (50.8 μm pitch) as many as 72 fibers arranged in a square array (83 when a hexagonal array is utilized) fit above a single 50.8×50.8 μm pixel of sensor 55 and therefore alignment of the FOP may not be critical. Though a FOP 60 is illustrated in FIG. 8, other technology may be substituted for the FOP to achieve the same results by serving as a directional filter, such as a micro-louver based structures such as Vikuiti™ Light Control Films manufactured by 3M (St. Paul, Minn., U.S.A). Other optics capable of restricting the propagation of incoming light to that representative of the fingerprint topology may also be used. Other than the use of the ambient light reducing components (e.g., FOP 60) in sensor 54, the operation of light sensing pixels 24 and other electronics of array 55 may be the same as described earlier in connection with FIG. 2.

Figure 9:
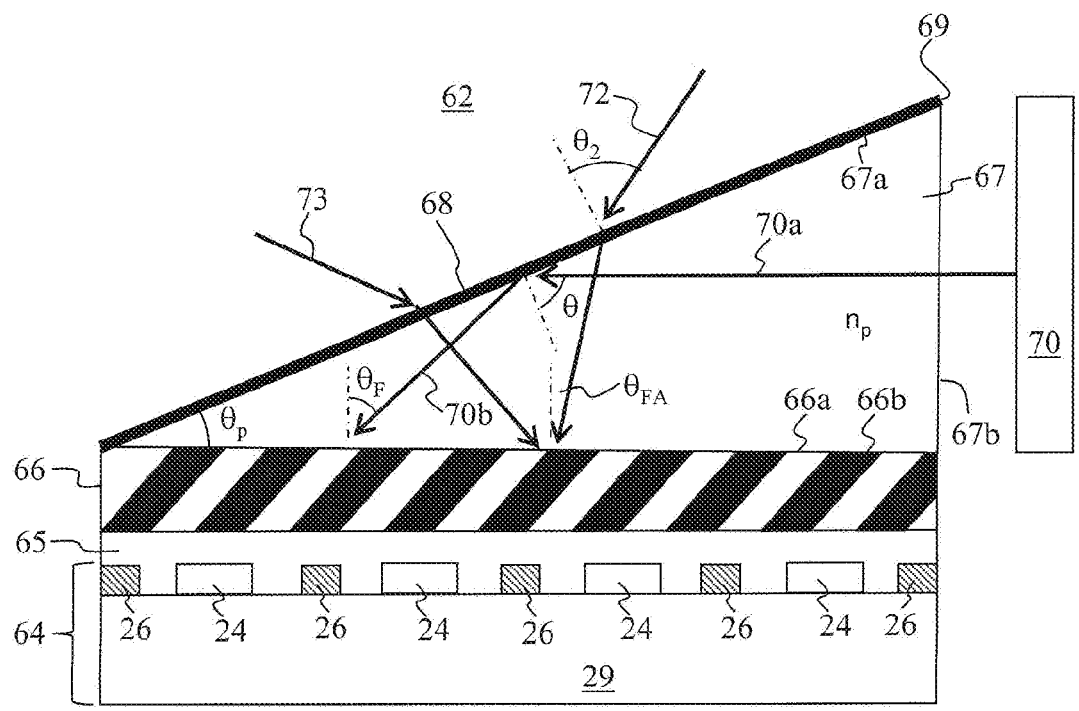
FIG. 9 is a schematic cross-section of a portion of 2D TFT-based sensor in accordance with a seventh embodiment of the present invention showing front light illumination and a prism for TIR illumination, a coating and a tilted fiber-optic plate (FOP) for ambient light rejection.

Referring to FIG. 9, a seventh embodiment of the present invention of a non-imaging contact sensor 62 with a sensor array 64 and protective coating 65, which may be the same or similar to sensor array 22a and coating 27 described earlier, having a FOP 66 that where the fibers of said FOP are not collinear with the surface normal of array 64. Rather, the fibers 66a and absorbing regions 66b of the FOP 66 are oriented in a desired direction according to the direction the light reflected (light 70b) from the fingerprint platen 68 will be propagating at. A prism 67 of index of refraction $n_p$ is provided having along one face providing a platen 68 finger contact surface. As will be described below, optionally face 67a has coating layer 69 where the top surface thereof provides platen 68. Illumination is provided by a light source 70 similar to light source 21 but aligned parallel to surface 67b facing the light source, so as to provide light 70a which reflects off platen 68 by TIR as light 70b representative of finger topology at an angle aligned with fibers 66a so that the light passes substantially along the axis of such fibers so as to reach light sensing pixels 24. Ambient light 72 and 73 when incident platen 68 enters prism 67 at an angle which is not aligned with fibers 66a and therefore is blocked by FOP 66 from reaching sensor array 64, i.e., the ambient light is absorbed by regions 66b before it reaches light-sensitive areas 24. Other than the use of the ambient light reducing components (e.g., prism 67, FOP 66, coating 69) of sensor 62, the operation of light sensing pixels 24 and other electronics of array 64 may be the same as described earlier in connection with FIG. 2.

Note that for FOPs 60 and 66 of FIGS. 8 and 9 their numerical aperture (NA) of the fibers are ideally as small as possible and in such a manner allow only a small cone angle of light about the propagation angle of the fingerprint illumination 70a to be guided as light 70b towards the light sensing pixels 24. Light propagating at angles outside of the acceptance cone of the fibers 66a will not be guided and will propagate through the fibers 66a and into the interstitial layers along the fibers that are preferentially absorbing. Having a small NA also minimizes crosstalk (e.g., light from one fiber spilling across several light-sensitive areas 24 in the course of traversing protective layer 65) from radiation as the light 70b emerges from the end of fibers 66a and heads towards the light sensing pixels 24. For example, FOP 66 may be manufactured by Schott North America Glass (Southbridge, Mass.) with 55A fibers that contain interstitial absorbing fibers and has an NA=0.28. In air this NA translates to an acceptance cone of ±16.3° (±10.8° for a fiber immersed in an adhesive or protective layer with an index of refraction of 1.5). To illustrate how such a low-NA fiber can be used to block ambient, consider the case where the platen incident angle is θ=65° and the index of refraction of the prism is $n_p$=1.5. The critical index of the device defined by $n_p \cdot \sin \theta$=1.36 which is greater than the 1.33 of the index of refraction of water, thereby making such a system water-rejecting (as defined by U.S. Pat. No. 5,416,573). Further, if the prism angle is set to $\theta_p=25°$, then the angle of incidence the reflected fingerprint light 70b will make with the FOP 66 is $\theta_F=40°$. Looking at the ambient light 72 coming into the prism 67 with an angle of incidence of $\theta_2$, even if the ambient light 72 comes in at a grazing incidence (i.e., $\theta_2=90°$), the maximum angle of the ambient light at the FOP is $\theta_{FA}=16.8°$, which is outside of the FOP 66 acceptance cone angle of 40±10.8°=29.2° to 50.8° and therefore will be blocked by the interstitial absorbing glass lining fibers 66a of the FOP 66.

If the only changed parameter of the previous example is the prism 67 illumination geometry of FIG. 9 such that the platen 68 angle of incidence changes to $\theta=45°$ instead of 65°, then the critical index becomes $n_c=1.06$ and the sensor 62 still operates in TIR, but air-rejecting and not water-rejecting as was previously the case. The light reflected 70b off of the platen 68 now makes an incident angle of $\theta_F=20°$ on the FOP 66. If ambient light 72 is at grazing incidence as before (i.e., $\theta_2=90°$), the angle of the ambient light at the FOP 66 is still at $\theta_{FA}=16.8°$, which is inside the FOP acceptance cone angle of 20±10.8°=9.2° to 30.8°. In order to drop outside of the FOP acceptance angle, the ambient light 72 must have an incident angle $\theta_2$ of 59° or less. This may be accomplished using a light shield of FIG. 5, but can also be accomplished by coating 69 providing the platen 68 surface. As discussed earlier, coating 69 may comprise of dielectric layers, holograms, or a combination thereof. The coating 69 would then be preferentially exhibit high-reflectivity for ambient light 72 at wavelengths used by the fingerprint scanner and for incident angles of $\theta_2>59°$.

In summary, sensors 54 and 62 each has a directional filter provided by FOP 60 and 66, respectively. An issue with ambient light is that it tends to enter into the contact fingerprint sensor at all angles. In particular when ambient light is outside light, the ambient light can essentially come in across $2\pi$ steradians. To filter this light, several technologies can be used. For example holographic technology can be used to let pass the fingerprint sensing illumination propagating at specific range of angles, polarization, and wavelengths, and block light (such as ambient light) that is outside of these specification ranges. Alternately or in parallel, a fiber-optic faceplate (FOP) sensors 54 and 62 can be used.

Figure 10:
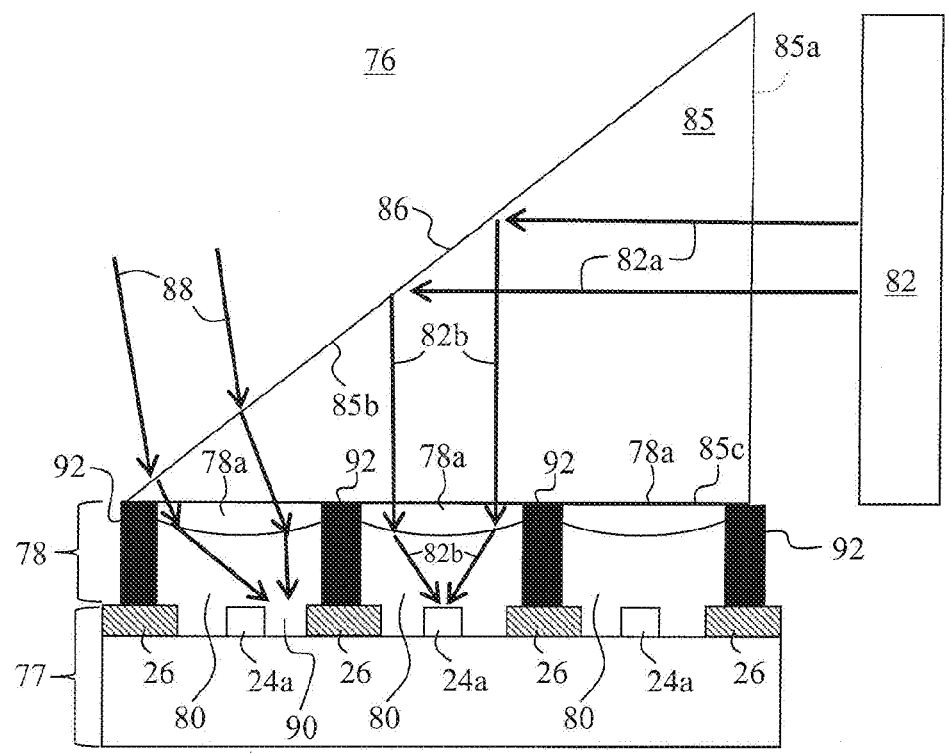
FIG. 10 is a schematic cross-section of a portion of 2D TFT-based sensor in accordance with an eighth embodiment of the present invention showing front light illumination and a microlens arrays to limit the FOV of ambient light that affects the light sensing pixels of the sensor.

Referring to FIG. 10, an eighth embodiment of the present invention of a non-imaging contact sensor 76 with a sensor array 77 having an array 78 of micro-optics 78a (microlenses or other optical structures) which reduces the effect of ambient light. Sensor array 77 may be the same or similar to sensor array 22a, but with region 80 which may be air or may contain a material that protects array 77. Microlens array 78 in conjunction with a small fill factor of array 77, as provided for as described in the second embodiment, are utilized to reduce the effect of ambient light. The small fill factor being illustrated by smaller light sensing pixels 24a than light sensing pixels 24 which provide the same function as light sensing pixels 24 over a smaller light receiving area.

Figure 11:
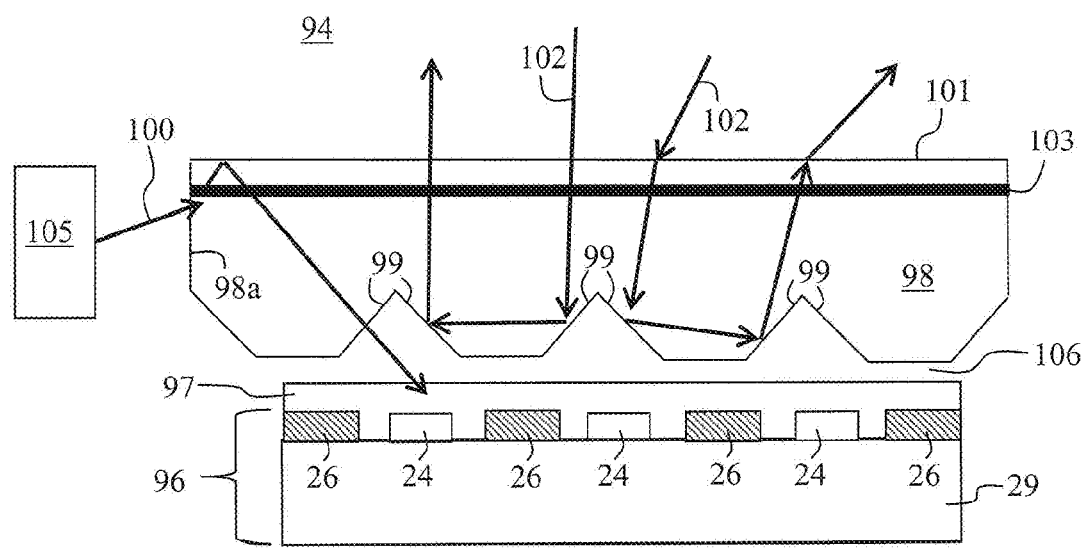
FIG. 11 is a schematic cross-section of a portion of 2D TFT-based sensor in accordance with a ninth embodiment of the present invention showing front light illumination and a lenticular array of a prism type structure to limit the effect of ambient light on the light sensing pixels of the sensor.

Illumination is provided by a light source 82 similar to light source 21, but aligned parallel to face 85a of a prism 85 to provide light 82a which reflects off platen 86 provided by face 85b of prism 85 by TIR to provide light 82b representative of finger topology aligned substantially normal to face 85c (and/or substantially normal incident to the light sensing area of light sensing pixels 24a) which is then focused by the two-dimensional array of microlenses 78a aligned relative onto their respective active light sensing area of light sensing pixels 24a. The field of view of each of microlenses 78a is over the active light sensing pixel area for its associated light sensing pixel element 24, such as illustrated for example by light 82b. Light 88 that enters microlens array 78 at an oblique angle (by way of prism 85), however, is focused off to the side 90 of the light sensing pixel 24a and therefore not detected by the light sensing pixel 24a. Although the micro-optics 78a are illustrated preferentially aiding in the detection of normally incident light, the microlens-pixel relative alignment can be changed such that light incident at a non-normal incidence such as 30 degrees is preferentially detected. Optionally the microlens array 78 may contain light barriers 92 to further assist in the prevention of ambient light from propagating (reflecting, refracting or scattering) into neighboring light sensing pixels 24a. Thus, the micro-optics 78a limit the field-of-view (FOV) seen by the sensor array 77. Other examples of micro-optics that may be designed for FOV limitation include lenticular arrays such as shown in FIG. 11, Fresnel optics, micro-prism arrays, etc. Other than the use of the ambient reducing components (e.g., prism 85, array 78, and light barriers 92) of sensor 76, the operation of light sensing pixels 24a and other electronics 26 of array 77 may be the same as described earlier in connection with FIG. 2 with light sensing pixels 24.

Referring to FIG. 11, a ninth embodiment of the present invention of a non-imaging contact sensor 94 with a sensor array 96 having micro-optic that is a lenticular array of microprisms 98 to control the effect of ambient light. Sensor array 94 may be the same or similar to sensor array 22a, but with protective coating 97. As illustrated, the microprism 98 structure is aligned relative to the light sensing areas of light sensing pixels 24, such that only light 100 from platen 101 coming substantially normal to the prism facets 99 are transmitted onto light sensing pixels 24. If the prism facets 99 are cut at a 45 degree angle, the medium 106 between protective layer 97 and the microprism structure 98 is air, and the plastic is polycarbonate with an index of refraction of 1.59, then only ambient light 102 that has an angle of incidence at the platen 101 of >9.6 deg can be detected by light sensing pixels 24 of sensor 94. By adding coatings to the prism surface as well as orienting the microprism at a particular distance from the sensor pixels, the amount of ambient light that is detected by sensor pixels 24 may be further reduced. Other than the use of the ambient reducing components (e.g., microprisms 98) of sensor 94, the operation of light sensing pixels 24 and other electronics of array 96 may be the same as described earlier in connection with FIG. 2. Although the microlenses 78a or lenticular array 98 are shown, other micro-optics may be similarly used for FOV limitation, such as Fresnel optics. As illustrated in FIG. 11, the illumination light source 105 is oriented such that fingerprint illumination light 100 is directed at facet 98a of microprism array 98. With such edge illumination, one typically encounters a TIR condition between the platen 101 and the skin placed on the platen. To eliminate this, one may utilize a hologram 103 that diffracts the light 100 up towards the platen 101 at a non-skin TIR angle (but it maybe still be TIR for air or for water, or not TIR at all depending upon how the microprism geometry in terms of its ability to pass fingerprint illumination wavelengths and reject ambient light).

Figure 12:
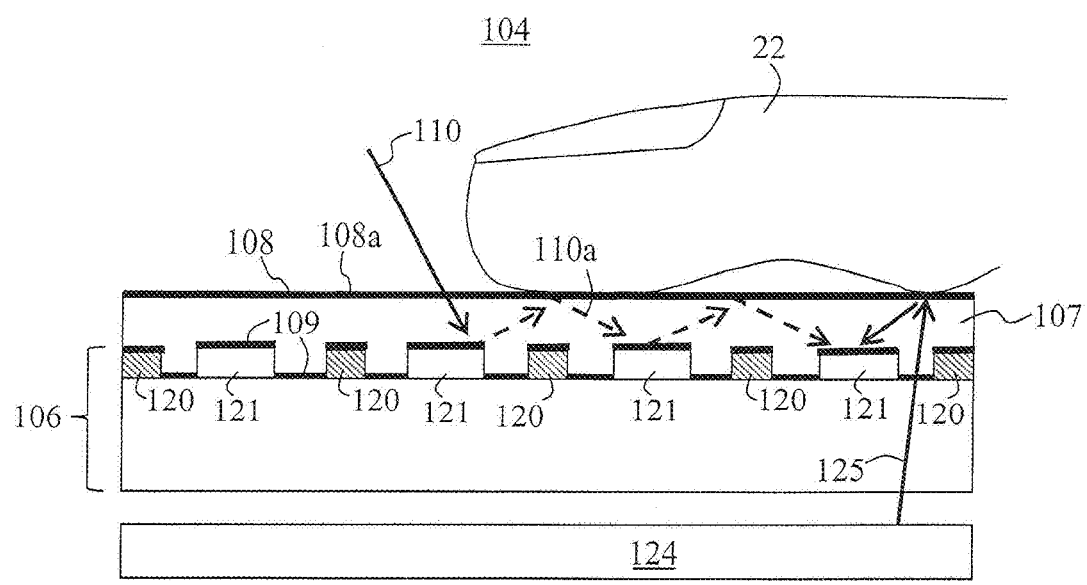
FIG. 12 is a schematic cross-section of a portion of 2D TFT-based sensor in accordance with a tenth embodiment of the present invention having coatings to minimize effect of ambient light "tunneling" underneath the finger and exposing sensor pixels that should otherwise be shadowed from ambient light.

Referring to FIG. 12, a tenth embodiment of the present invention of a non-imaging contact sensor 104 with a sensor array 106 having a protective coating 107, and then additional coatings or layers 108 and 109 to minimize the effect of ambient light scatter. Sensor array 104 and coating 107 may be the same or similar to sensor array 22a and coating 27. A platen 108a is provided by the surface of coating 108. As described earlier, sensors fabricated using TFT, CMOS, or other technologies, are susceptible to ambient light scattering and reflecting underneath inside of the protective layer 107 and in this manner tunneling underneath the finger, thereby exposing sensor pixels 24 that would otherwise be shadowed from ambient light. By incorporating coating 108, coating 109, or a combination of the two, the tunneling of ambient light 110 can be mitigated. Coating 108 is an antireflection (AR) coating that reduces the reflection coefficient from the material above the protective coating 107, for example air, and the material of the protective coating 107 itself. Preferentially this AR coating 108 (for example fabricated with dielectric coating layers) is tuned for the wavelengths, polarizations, and angles of incidence that the tunneling effect is magnified by. Coating 109 is also an AR coating, but the coating need not be perfectly smooth. Instead the coating may be structured in order to enhance absorption of light by the light sensitive pixel elements 121. An example of such a structured coating can be found in Li Chen et al, SPIE Proceedings Vol. 7046 (2008). It is the goal of coating 109 to suppress as much incident light as possible such that as much incident light enters into the active areas of light sensing pixels 121 as possible and does not spread (e.g., reflect or scatter) to neighboring pixels as illustrated by the dashed arrows 110a. Other than the use of the ambient reducing components (e.g., coatings 108 and 109) of sensor 104, the operation of light sensing pixels 121, transistors 120, and other electronics of array 106, and light source 124 may be the same as described earlier in connection with FIG. 2.

Figure 13:
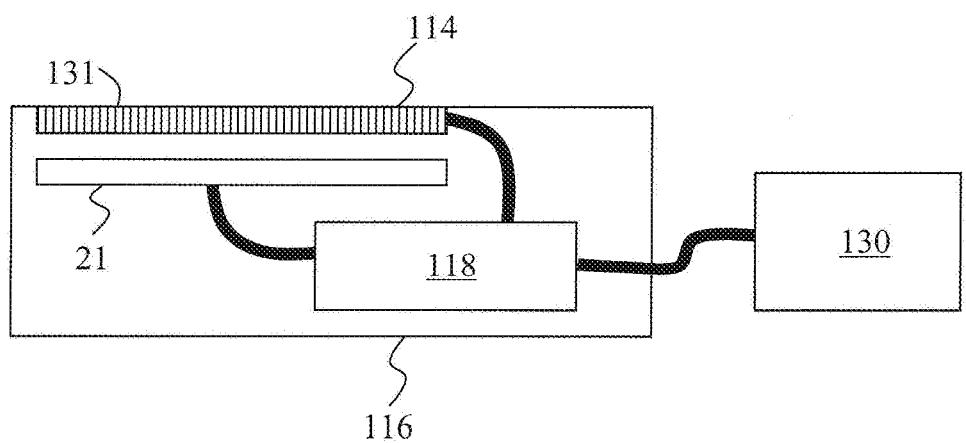
FIG. 13 is a block diagram of a fingerprint scanner system using a TFT-based sensor with light rejection in accordance with one or more of embodiments of the present invention.

FIG. 13 is a block diagram of a fingerprint imaging apparatus or system 112 using the non-contact sensor 114 having the ambient light blocking components of one or more of sensors 30, 37, 54, 62, 76, 94, or 104, or reduce fill-factor light sensing pixels 24 and/or spectral wavelengths for illumination and detection outside ambient spectra (FIGS. 6 and 7) or spectral filter of the fifth embodiment. A housing 116 is provided having an aperture or opening for locating sensor 114, where the surface of sensor 114 provides a platen 131, and such sensor 114 uses back-light illumination source 21, or without illumination source 21 and platen 116, in which a prism 67 or 85 or other optical element is provided in apparatus 112 with front light illumination 70 or 82, and platen 68 or 86, is provided when sensor 62 or 76, respectfully are used. Signals representative of a two-dimensional fingerprint(s) are processed by processor 118 to provide a fingerprint image to computer 130 for fingerprint identification, verification, or enrollment. Computer system 130 also has a display and user interface (e.g., keyboard, touch screen or mouse) and represents a computer system typical of a fingerprint imaging apparatus, and is programmed to control the operation of apparatus 112 for capturing fingerprints. Optionally a light shield 46 may also be used, if desired.

It should be understood that the word fingerprint or finger is meant to refer to not just a fingerprint or a finger but rather to any skin topology and any type or portion of skin (for example fingers, thumbs, palms, toes, etc.). Such skin upon platen 68, 86, 101 for respective sensors 62, 76, or 94 may be, for example 10 mm, from respective sensing pixels 24 or 24a, particularly when spatially and temporally coherent light is generated by light sources 70, 82, and 105. In other sensors 30, 37, 54, and 104, the skin upon respective platen 35, 44, 57, and 108a can be proximate to respective sensing pixels 24 and 121, such as 1 mm or less, so long as light representative of skin topology in contact with the platen can be received by sensing pixels and then signals there from readout by electronics as a captured image suitable for biometric applications. Additionally, arrays 31, 40, 55, 64, 77, 96, and 106, having respective sensing pixels 24, 24a, and 121 are shown as including the backplane substrate 29, however such arrays and their associated electronics may be considered as being disposed on the front surface of the substrate 29 as shown in the figures and not inclusive of the substrate.

Although the sensors in the above embodiments are two-dimensional (2D), the sensors may instead be one-dimensional (1D) sensors (commonly called line sensors), which may also be effected by ambient light in the same manner are described earlier in the background section for 2D sensors. Accordingly, the embodiments above providing reduction or elimination of ambient light are also applicable to 1D non-imaging contact fingerprint sensors as well.

Further, although the seventh through ninth embodiments (FIGS. 9-11) have non-imaging contact sensors which utilize front light illumination of their respect platen surfaces, they may alternatively use back light illumination. Also, the first through fifth and tenth embodiments may utilize front light illumination. In other words the embodiments described herein need not be deemed reliant on the manner in which the platen is illuminated; even through the particular illumination shown in the figures is preferred.

From the foregoing description, it will be apparent that there have been provided improved non-imaging contact finger print sensors. Variations and modifications in the herein described sensors, and methods of use will undoubtedly suggest themselves to those skilled in the art. Accordingly, the foregoing description should be taken as illustrative and not in a limiting sense.

The invention claimed is:

1. A sensor for capturing images of skin topology while restricting entry of ambient light into the sensor, comprising:
   a platen;
   a one or two-dimensional array of light sensing pixel elements that are configured for receiving light representing skin topology, said light representing a surface topology of a portion of skin tissue that is disposed upon said platen; and
   a directional filter comprising a plurality of passageways that each have two opposite ends, and wherein each of said passageways has at most two openings that are each located at either of said two opposite ends, and wherein said directional filter is configured so that light can only pass into or through said directional filter via passage through at least one of said openings; and wherein light is further restricted from passing into any one of said passageways, unless such light passes through at least one of said openings via an acceptance cone that is associated with at least one opening of one passageway; and wherein
   said directional filter is disposed between said platen and said array of light sensing pixel elements, and wherein said directional filter is further configured to allow passage of light from said platen towards said array of light sensing pixel elements, and further configured to allow passage of light from a source of non-ambient light that passes through said array and towards said platen.

2. The sensor of claim 1 wherein a light absorbing material is disposed within said directional filter and in between said passageways.

3. The sensor of claim 2 wherein the light absorbing material is black glass.

4. The sensor of claim 1 including a coating material that is configured for blocking one or more ranges of wavelengths of ambient light for which said light sensing pixel elements are sensitive to.

5. The sensor of claim 1 wherein each passageway is aligned to transfer light to a location of one of said light sensing pixel elements.

6. The sensor of claim 1 wherein the passageways are arranged into one or more groups, and where each group is aligned to transfer light to a location of one of said light sensing pixel elements.

7. The sensor of claim 1 where the directional filter is a fiber optic plate.

8. The sensor of claim 1 wherein the directional filter is a set of micro-louver based structures.

9. The sensor of claim 1 wherein said light sensing pixel elements are disposed upon a substrate and said light sensing pixel elements each comprise a photo-detector element and comprise a switching element for reading signals representative of light detected by said photo-detector element.

10. The sensor of claim 9, wherein said switching element is a thin film transistor (TFT).

11. The sensor of claim 1, wherein said light sensing pixel elements are disposed on a substrate, and said sensor further comprises a source of non-ambient light that is configured for illuminating said substrate at one or more ranges of wavelengths of light for which said light sensing pixel elements are sensitive to.

12. The sensor of claim 1, wherein said light sensing pixel elements are configured to operate to sense light at one or more ranges of wavelengths of light having reduced power within an ambient light spectrum, and said substrate is illuminated by non-ambient light of said at said one or more ranges of wavelengths.

13. The sensor of claim 1, wherein each of said light sensing pixel elements occupies an overall area in which a physical portion of said overall area operates to receive said light representative of skin topology, and said portion of said overall area is of a size selected to reduce sensitivity of said light sensing pixel elements to ambient light illumination while enabling said light representative of skin topology to still be sensed by said light sensing pixel elements.

14. The sensor of claim 1, wherein said light sensing pixel elements are disposed upon a substrate along with other electronics enabling operation of said light sensing pixel elements and said sensor further comprises a protective layer of material over said substrate, in which said directional filter is affixed to said protective layer.

15. The sensor of claim 14, further comprising material upon at least said light sensing pixel elements and said other electronics in which said material reduces scattering of said ambient light.

16. The sensor of claim 1 wherein said light received by said light sensing pixel elements is unmagnified, which is equivalent to a magnification value of one to one (1:1).

17. A sensor for capturing images of skin topology comprising:
a platen;
a directional filter that is disposed between said platen and an array of light sensing pixel elements, said directional filter including passageways providing for passage of light from said platen and towards said array of light sensing pixel elements and providing for passage of light from a source of non-ambient light that passes through said array and towards said platen, and wherein
each of said passageways is restricted to having two and only two openings at opposite ends of each passageway, and wherein light traveling from said platen, and light traveling from said source of non-ambient light are each restricted from traveling through any pathway other than said passageways of said directional filter; and wherein
light is further restricted from passing into any one of said passageways, unless such light passes through at least one of said openings via an acceptance cone that is associated with at least one opening of one passageway; and
said array of light sensing pixel elements being configured for receiving light representative of skin topology, wherein each of said light sensing pixel elements collectively occupy a portion of an overall area,
and wherein said portion is of a size that is limited to being less than 40% of said overall area.

18. The sensor of claim 17, wherein said size is limited to being less than 30% of said overall area.

19. The sensor of claim 17, wherein said size is limited to being less than 20% of said overall area.

20. A method for capturing images of skin topology comprising the steps of:
providing a platen;
providing a one or two dimensional array of light sensing pixel elements;
providing a source of non-ambient light;
providing a directional filter that is disposed between said platen and an array of light sensing pixel elements, said directional filter including passageways providing for passage of light from said platen and towards said array of light sensing pixel elements and providing for passage from light from said source of non-ambient light that passes through said array and towards said platen, and wherein
each of said passageways is restricted to having two and only two openings at opposite ends of each passageway, and wherein light traveling from said platen, and light traveling from said source of non-ambient light are each restricted from traveling through any pathway other than said passageways of said directional filter; and wherein
said array of light sensing pixel elements is configured for receiving light representative of skin topology in which said light sensing pixel elements collectively occupy a portion of an overall area; and
and wherein said portion is of a size that is less than 40% of said overall area.

* * * * *